United States Patent [19]
Chen et al.

[11] Patent Number: 5,187,981
[45] Date of Patent: Feb. 23, 1993

[54] ULTRASOUND TRANSDUCER

[75] Inventors: James N. C. Chen, Chelmsford; Susan Ostrowski, Stoneham, both of Mass.

[73] Assignee: Hewlett-Packard Company, Palo Alto, Calif.

[21] Appl. No.: 667,858

[22] Filed: Mar. 12, 1991

[51] Int. Cl.⁵ .......................... G01N 29/24; A61B 8/14
[52] U.S. Cl. .................................. 73/642; 128/663.01
[58] Field of Search ................ 73/603, 606, 620, 625, 73/626, 627, 629, 632, 642, 644; 128/660.01, 660.07, 661.01, 662.03, 663.01

[56] References Cited
U.S. PATENT DOCUMENTS

| | | | |
|---|---|---|---|
| 3,958,559 | 5/1976 | Glenn et al. | 128/663.01 |
| 4,248,090 | 2/1981 | Glenn | 128/663.01 |
| 4,700,575 | 10/1987 | Geithman et al. | 73/642 |
| 4,794,930 | 1/1989 | Machida et al. | 128/662.03 |

Primary Examiner—Hezron E. Williams
Assistant Examiner—Rose M. Finley
Attorney, Agent, or Firm—Frank R. Perillo

[57] ABSTRACT

A transducer assembly, suitable for medical examinations, for generating an apodized sector shaped beam of energy. A transducer in the form of a crystal, has a ring-like structure on its face which apodizes the signal produced by the transducer by providing a greater amount of attenuation at the transducer's periphery than at the transducer's center.

2 Claims, 4 Drawing Sheets

ULTRASOUND TRANSDUCER

BACKGROUND

Ultrasound scanning is finding increased usage in the examination of the peripheral vascular (PV) structure of the human body. Both sector and linear scanning may be used, and each form of scanning may be generated by mechanical or electronic scanners. The PV target area may be illuminated by bursts, or continuous waves of ultrasound energy, depending on the parameters to be measured. In either case, a beam plot of the transmitted wave would show a beam, generally centered at the middle of the transducer, having a region of high energy or high sensitivity at its center. Moving off of the center of this beam, the plot would show regions of lower energy or sensitivity. Such lower sensitivity portions of the transmitted beam might include sidelobes. A similar beam plot could be constructed for received energy.

The vessels to be examined as part of a PV scan are often near the surface of the subject's body. When sector scanning is used for such an examination, it is necessary to have the transducer be some distance from the skin surface of the subject. This is due to the "fan-shaped" nature of the sector scan. If the sector scanner were held against the subject's skin, only a small portion of the beam would intersect the PV region of interest. Holding the sector scanning transducer off the skin affects the beam in two ways. First, the beam becomes wider at the intersection of the region of interest. In addition, the effects of ring down noise caused by the generation of the transmitted pulse are reduced.

If the sector scanning transducer were simply held off the subject's skin, with nothing but air between the transducer and the subject, there would be an inefficient coupling of ultrasonic energy into the region of interest. To prevent this inefficient energy transfer, stand-off devices are commonly used to place the sector scanning transducer at the right position and efficiently couple energy to the region of interest. One such device is described in U.S. Pat. No. 4,579,123, assigned to the assignee of the present application. Stand-off devices may be separate structures, to which a transducer is mechanically or acoustically coupled, or the device may be an integral part of the transducer structure.

SUMMARY OF THE INVENTION

When stand-off devices are used with a sector scanning transducer, it has been noticed that artifacts in the form of multiple echoes or "ghosts" often appear on the display screen when a subject or a test target is being examined. The present invention resides in a recognition of this problem, the discovery of its source, and the development of a structure that reduces or eliminates the effects of this problem. It is believed by the inventors that the ghosts referred to above occur because of reflections of the low sensitivity portions of the transmitted beam off the inside walls of the stand-off device, resulting in multipath illumination of the target area. Since these multipath reflections take longer to reach a particular point on the target than does the direct illumination of this point by the high energy portion of the beam, multiple echoes or ghosts of this point appear on the display. Such multipath reflections also may occur during reception. An apodizing structure is inserted in the radiation path of the transducer that decreases the intensity of the beam in the regions of the beam that produce these multipath reflections, thereby significantly reducing or even eliminating the ghost artifacts.

DETAILED DESCRIPTION OF THE PREFERRED EMBODIMENT

In the following description, corresponding components in the various figures of the drawings are designated in the same way.

Figure 1:
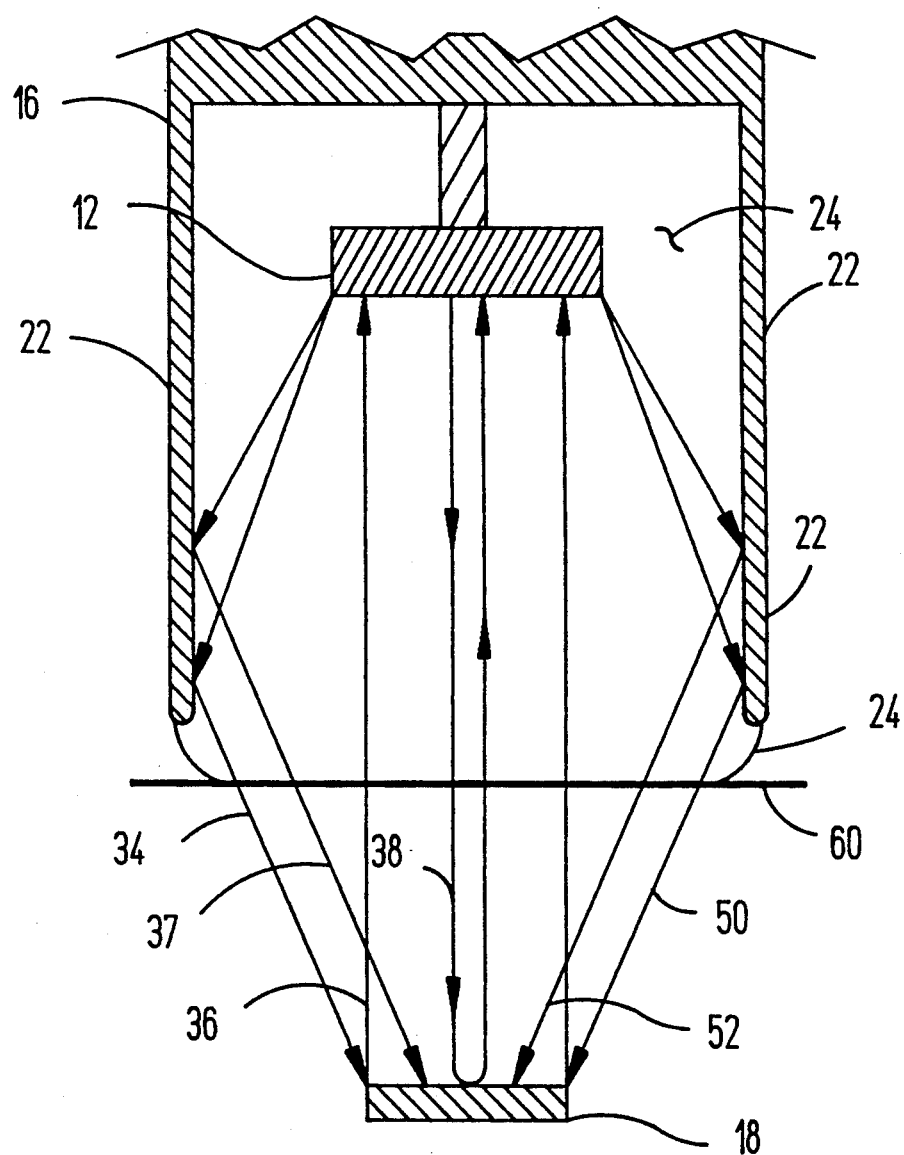
FIG. 1 is a simplified cross-sectional view of a portion of an ultrasound transducer and stand-off assembly, illustrating the problem solved by the present invention.

Referring to FIG. 1, element 10 is a combined mechanically scanned ultrasound transducer and stand-off assembly known in the prior art. Transducer crystal 12 is separated from the target 18 by the wall 22 of structure 10. Wall 22 is generally cylindrical in shape and is coupled at one end to the housing. The other end of the wall assembly is covered by window 20, thereby completely enclosing the transducer. Window 20 is essentially transparent to ultrasonic energy. When a subject or patient is being scanned, target 18 will be below the surface 60 of the subject's skin. Coupling of the ultrasound energy to target 18 is facilitated by fluid 24, which fluid may be a water/glycol mixture.

Figure 2:
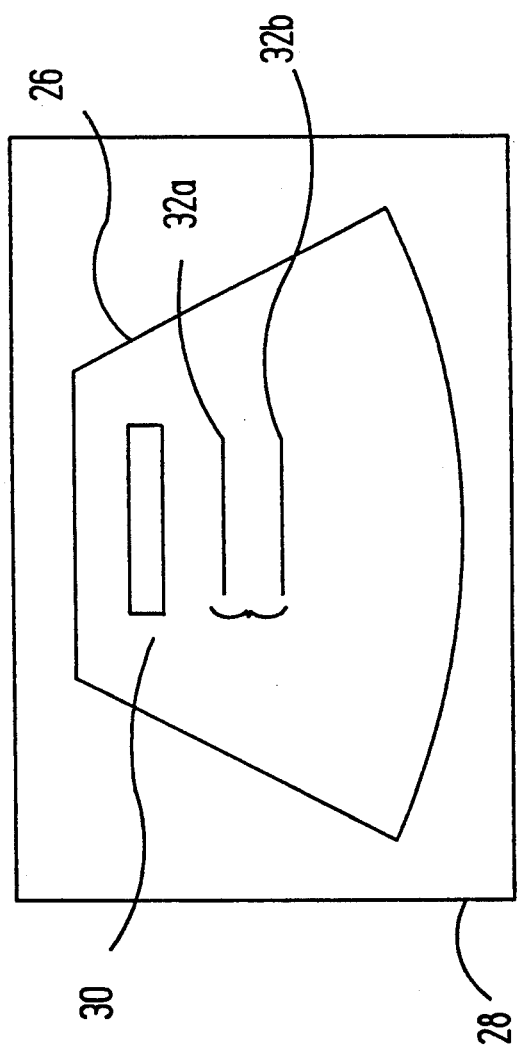
FIG. 2 is a representation of a screen display produced by the structure of FIG. 1 showing the ghost artifact.

In the operation of the structure of FIG. 1, assume that crystal 12 is energized, and oscillated by a drive mechanism along a plane that is at right angles to the surface of the drawing, thereby illuminating the target with a sector shaped pattern of ultrasonic energy. This sector scan 26 appears on display screen 28 in FIG. 2. Structure for energizing and oscillating crystal 12 are contained in housing 16, not fully illustrated. These structures are well known in the art and form no part of the present invention.

Within sector scan 26 is a representation 30 of target 18. Also shown are examples of artifacts 32a, 32b in the form of weaker versions, or ghosts, of target 18. When crystal 12 is energized, for example, to produce a burst of ultrasonic energy, the target 18 is illuminated by energy from the center of the beam. This energy, represented in part by lines 36 and 38, is reflected back to crystal 12 to produce target image 30. It is believed that ultrasonic energy from the lower sensitivity portions of the transmitted beam represented in part by lines 34, 37, 50 and 52 is reflected off the inside surface of stand-off walls 22 to illuminate target 18 with energy arriving at times later than the energy from the center of the transmitted beam. Because the paths travelled by lines 34, 37, 50 and 52 are longer than the path travelled by lines 36 and 38, additional ghost target images 32a and 32b will be displayed at apparent depths greater than the depth of target 18.

Figure 3:
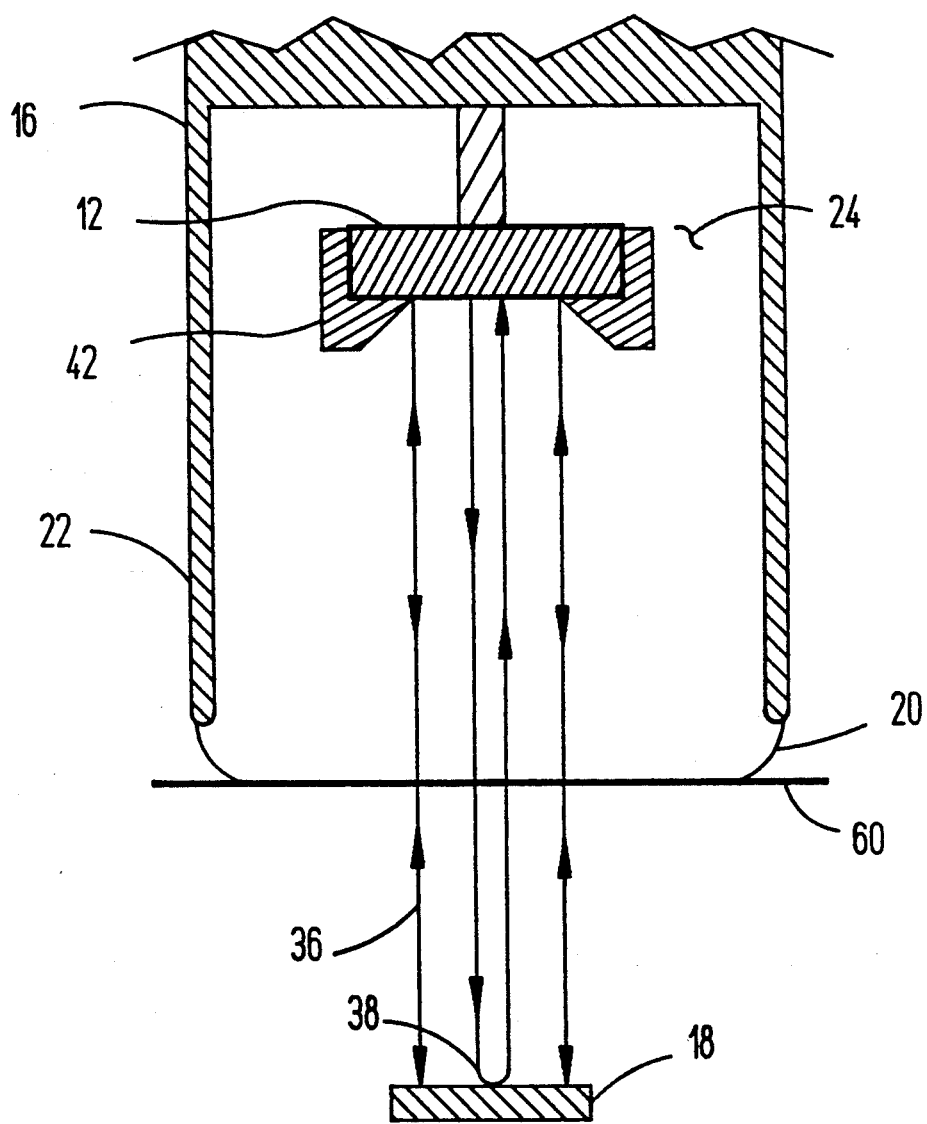
FIG. 3 is a simplified cross-sectional view of a portion of an ultrasound transducer constructed in accordance with the invention.
Figure 4:
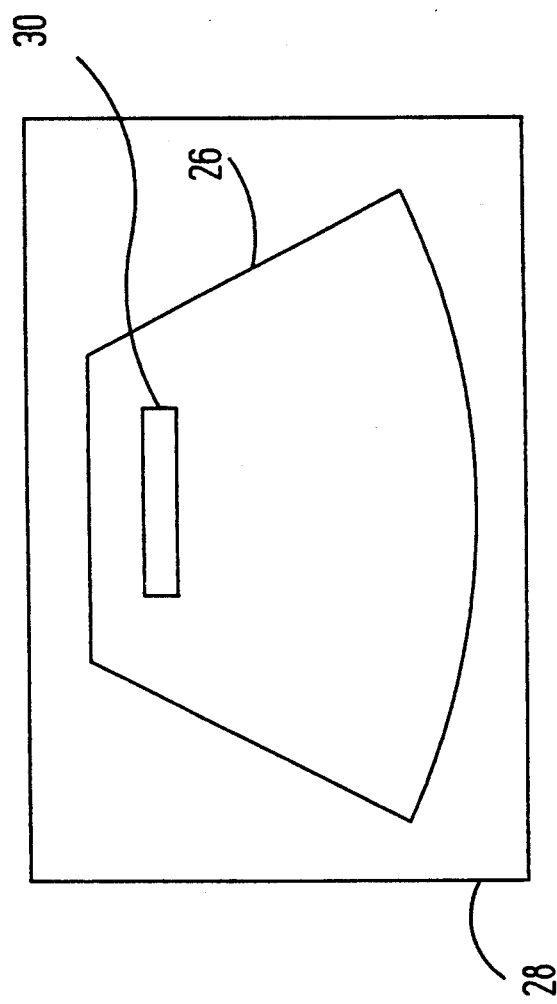
FIG. 4 is a representation of a screen display produced by the structure of FIG. 3 showing the elimination of the ghost artifact.

FIG. 3 shows a modification of the structure of FIG. 1 to reduce or eliminate the previously discussed ghost artifacts. An apodizing structure 42 in the form of a ring-like assembly is added to the periphery of crystal 12. This ring is made from a material that will attenuate ultrasound energy. The attenuation profile of apodizing structure 42 is chosen to provide more attenuation at the periphery of crystal 12 than in the center. In the preferred embodiment, there is no attenuation provided by 42 in the center region of crystal 12. A taper was chosen from the edge of structure 42 towards the center of crystal 12 to provide a gradual attenuation of the beam. Although not necessary to practice the present invention, structure 42 has been designed to cover the ends of crystal 12 as a means of attaching it to the crystal and to attenuate any signals that might radiate from the ends of crystal 12 due to unwanted vibration modes.

To minimize internal reflections, structure 42 is made from a material having acoustic properties similar to those of fluid 24. In the preferred embodiment, structure 42 is made of Santoprene 101-80 brand polyolefin, manufactured by Monsanto. Energy illuminating target 18 is represented in part by lines 36 and 38. Note that because of structure 42, reflections of energy off of the inside surface of stand-off walls 22 have been eliminated or greatly reduced. As a result, target 18 is displayed on display 28 as a single clean image 30, representing the actual target configuration. Ghost artifacts 32a and 32b have been eliminated or greatly reduced.

Crystal 12 as shown in FIG. 3 may have the same dimensions as the corresponding element in FIG. 1. However, since structure 42 decreases the effective radiating area of crystal 12, it may be desireable in practice to utilize a larger crystal when a ring is used, to yield the same effective radiating surface as that of a crystal used without such a ring.

While this invention has been particularly shown and described above with references to specific embodiments, the foregoing and other changes in form and detail may be made by one skilled in the art without departing from the spirit and scope of the invention, as defined in the appended claims. For example, a structure was disclosed which included a transducer and stand-off device constructed as a single assembly. Use of separate transducer and stand-off assemblies is within the scope of the present invention as is the use of an apodizing structure that was a separate structure or was part of the separate standoff device, so long as the apodizing structure was acoustically coupled to the transducer in an appropriate manner.

Apodizing structures having shapes other than rings may be used. For example, U.S Pat. No. 4,700,575 describes an apodizing layer. The article "Single-Transducer Electrode Design for Beam Shaping in Biomedical Ultrasound" by Harrison and Balcer-Kubiczek, IEEE Transactions in Ultrasonics Ferro Sections and Frequency Control, Vol. UFFC-33, No. 3, May 1986, describes the use of electrode shaping to achieve the desired beam profile. Either of these structures may be suitable for practicing the invention described herein.

Finally, while shown in conjunction with a mechanically scanned device, the teachings of the present invention may also be used in conjunction with electronically scanned transducers.

We claim:

1. An ultrasonic transducer assembly for illuminating a target with a sector shaped beam of ultrasonic energy comprising, in combination:
   a transducer housing open at one end;
   an ultrasound transducer coupled to said housing, capable of illuminating a target with a sector shaped beam pattern of ultrasonic energy and receiving reflections of ultrasonic energy from said target;
   a stand-off assembly for holding said transducer a predetermined distance from said target; and
   means for attenuating the ultrasonic energy generated by said transducer, said attenuating means comprising an apodizing structure have a ring-like shape, said structure covering the periphery, but not the center region of said transducer, whereby said attenuation is greater at the periphery of said transducer than at its center.

2. An ultrasonic transducer assembly for illuminating a target with a sector shaped beam of ultrasonic energy comprising, in combination:
   a transducer housing open at one end;
   an ultrasound transducer coupled to said housing, capable of illuminating a target with a sector shaped beam pattern of ultrasonic energy and receiving reflections of ultrasonic energy from said target;
   a stand-off assembly for holding said transducer a predetermined distance from said target; and
   means for attenuating the ultrasonic energy generated by said transducer by an amount that is greater at the periphery of said transducer than at its center, said means comprising an apodizing structure covering at least a portion of said ultrasound transducer, said structure being made from polyolefin.

* * * * *